United States Patent

Arraudeau et al.

[11] Patent Number: 5,223,559
[45] Date of Patent: Jun. 29, 1993

[54] COSMETIC COMPOSITION CAPABLE OF BLURRING SKIN DEFECTS

[75] Inventors: Jean-Pierre Arraudeau, Paris; Myriam Mellul, Vitry sur Seine; Didier Candau, Melun, all of France

[73] Assignee: L'Oreal, Paris, France

[21] Appl. No.: 842,649

[22] Filed: Feb. 27, 1992

[30] Foreign Application Priority Data

Feb. 28, 1991 [FR] France ................ 91 02400

[51] Int. Cl.$^5$ ................................ A61K 7/00
[52] U.S. Cl. ....................... 524/47; 424/63; 424/69; 424/78.03; 424/78.31; 424/401; 424/489; 424/499; 424/501; 424/502
[58] Field of Search ............. 524/47; 424/63, 69, 424/78.03, 78.31, 646, 641, 617, 489, 499, 501, 502, 402

[56] References Cited

U.S. PATENT DOCUMENTS

| | | | |
|---|---|---|---|
| 3,615,972 | 10/1971 | Morehouse | 156/79 |
| 4,164,563 | 8/1979 | Chang | 424/83 |
| 4,246,257 | 1/1981 | Elliott et al. | 424/78 |
| 4,414,200 | 11/1983 | Murphy et al. | 424/63 |
| 4,659,562 | 4/1987 | Arraudeau et al. | 424/63 |
| 4,820,510 | 4/1989 | Arraudeau et al. | 424/63 |
| 4,820,518 | 4/1989 | Murphy et al. | 424/401 |
| 4,839,163 | 6/1989 | Busch | 424/63 |
| 4,877,604 | 10/1989 | Schlossman | 424/64 |
| 5,023,075 | 6/1991 | Macchio et al. | 424/63 |

FOREIGN PATENT DOCUMENTS

| | | |
|---|---|---|
| 0056219 | 7/1982 | European Pat. Off. |
| 0106762 | 4/1984 | European Pat. Off. |
| 2612330 | 10/1976 | Fed. Rep. of Germany |
| 2367486 | 5/1978 | France |
| 2373277 | 7/1978 | France |
| 60-0255712 | 12/1985 | Japan |
| 61-69708 | 4/1986 | Japan |
| 90/04383 | 5/1990 | PCT Int'l Appl. |
| 2002652 | 2/1979 | United Kingdom |
| 1579934 | 11/1980 | United Kingdom |

Primary Examiner—Nathan M. Nutter
Attorney, Agent, or Firm—Oliff & Berridge

[57] ABSTRACT

A cosmetic composition contains a dispersion, in a fatty binder, of a particulate filler composed of solid particles of at least one material compatible with application to the skin. The particulate filler contains at least 50 wt. %, or at least 75 vol. % relative to the total particulate filler, of spherical or spheroidal particles 0.5 to 50 μ in size. The particulate filler has an oil uptake such that its concentration by volume C*, when the volume of binder is equal to that of the oil uptake (measured on the nonvolatile fraction of the binder), is between 3 and 90%. The concentration by volume of the particulate filler in the dispersion, measured on the nonvolatile fraction of the binder, namely without taking into account any volatile oils that may be present in the fatty binder, is at least equal to C* and preferably greater than C*. This composition allows skin defects (color differences and micro reliefs) to be blurred while leaving a translucent layer on said skin.

33 Claims, No Drawings

COSMETIC COMPOSITION CAPABLE OF BLURRING SKIN DEFECTS

A goal of the present invention is a cosmetic composition containing a powder dispersion able to blur defects of the skin such as microreliefs and changes in coloration.

BACKGROUND

A number of cosmetic compositions able to homogenize skin color and blur its relief, namely render variations in color and microreliefs of the skin, pores, and wrinkles less visible, has been proposed. These compositions are composed of powders dispersed in a binder. The powders generally contain colored pigments such as iron oxides and particulate additives such as mica or talc which are in the lamellar form, or silica in the platelet form. The effect is essentially achieved by means of the covering power provided by the lamellar additives; see for example U.S. Pat. No. 4,839,163.

A drawback to such compositions is that the blurring of the skin defects is provided by the covering power of the compositions, meaning that the composition applied to the skin is not translucent and does not confer a natural appearance on skin made up in this way. As a reminder, a makeup product is deemed to have covering power when it is able to mask imperfections in the skin by means of its opacity and/or its ability to reflect light. The use of lamellar additives has been considered as a way of increasing the impression of transparency (see also U.S. Pat. No. 4,839,163). In fact, however, lamellar additives act largely by reflecting light and for this reason have the disadvantage of conferring a somewhat unnaturally glossy appearance on the skin; see for example published Japanese application JP 61-69708, which proposes, as a remedy, preparing compositions wherein the particles of the additive are coated with an acrylic resin. A drawback to such compositions is that their preparation requires prior coating treatment whose integrity in the final formulation is not actually ensured.

Compositions have also been proposed which allow a film that masks wrinkles to be applied to the skin, these compositions containing in particular a water-soluble film-forming polymer, a plasticizer and a particulate additive such as a zeolite powder; see PCT WO 90/04383. The masking layer must in general be supplemented by a makeup layer. The skin receiving such an application does not have a natural appearance in this case either.

SUMMARY OF THE INVENTION

A goal of the present invention is a makeup product which blurs the relief of the skin although it contributes no particular covering power but on the contrary provides a translucent makeup layer conferring a natural appearance on the made-up skin.

It has been discovered that this goal and others may be achieved by the use of a powder dispersed in a fatty binder, by using a powder in the form of particles that do not have a platelet shape but on the contrary a spherical or spheroidal shape, through the use of specific binder-powder volume ratios.

One of the advantages of the invention is that the nature of the particulate material constituting the main powder particulate filler is not determinative, provided the material is compatible with application to the skin (i.e., nontoxic and nonirritant), and provided it is a material that yields white or faintly colored or spheroidal particles.

Hence a goal of the present invention is a cosmetic composition capable of blurring defects of the skin while leaving a translucent layer thereon, said composition comprising a dispersion, in a fatty binder, of a particulate filler composed of solid particles of at least one material compatible with application to the skin, characterized by the fact that said particulate filler contains at least 50 wt. %, or at least 75 vol. % relative to the total particulate filler, of spherical or spheroidal particles 0.5 to 50µ in size, that said particulate filler has an oil uptake such that its concentration by volume $C^*$, when the volume of binder is equal to that of the oil uptake (measured on the nonvolatile fraction of the binder), is between 3 and 90%, and by the fact that the concentration by volume of the particulate filler in said dispersion, measured on the nonvolatile fraction of the binder, namely without taking into account any volatile oils that may be present in the fatty binder, is at least equal to $C^*$.

In fact it has been discovered that a dispersion such as that defined above, when applied in a thin layer to the skin, is capable of blurring microreliefs and other defects of the skin while preserving the natural appearance of the skin due essentially to the translucent nature of this thin layer. In the above definition, the total particulate filler is composed of all the particulate filler, including any pigments present. The above condition relating to the spherical or spheroidal content of the particulate filler is that the particles must be present in a large proportion, generally equal to at least 50 wt. % of the additive. However, when the spherical or spheroidal particles are or include very light particles (as is the case for example for hollow particles of thermoplastic polymer containing a gas), these particles may be present in a large proportion by volume without their proportion by weight reaching 50%. In this case, the condition, for the compositions according to the invention, is that the proportion by volume of spherical or spheroidal particles be at least 75% relative to the total volume of the particulate filler.

DETAILED DESCRIPTION OF PREFERRED EMBODIMENTS

The invention relates in particular to compositions wherein the spherical or spheroidal particle weight content of the particulate filler is at least 75 wt. % or at least 80 vol. %, as well as to compositions for which this content is at least 85 wt. % or at least 90 vol. %.

It is known that the oil uptake of a powder varies not only with the material of which the powder is made but also with the nature of the oil component. Of course, for determination of the volume concentration C of the particulate filler, as well as for determination of $C^*$, the actual binder of the final composition is used, i.e. not only the nonvolatile fraction of the fatty binder proper, but also any oil-soluble ingredients present (for example surfactants when present) in the final cosmetic composition.

Usually, the particulate fillers used are such that the volume concentration $C^*$ is between 4 and 80%.

In the dispersion of the invention, the volume concentration C of the particulate filler, calculated as indicated above, is preferably such that the ratio between this concentration C and concentration $C^*$ is greater than 1, and in particular greater than or equal to 1.1.

It will be recalled that the oil uptake is measured by determining the volume Vh of the nonvolatile fraction of the fatty binder exactly necessary for filling the voids between the particles of the powder (additive). The oil uptake may be measured for example according to U.S. standard ASTM D281-84.

Let V be the volume of the particulate filler and V1 the volume of the nonvolatile fraction of fatty binder used in a given dispersion.

$$\frac{V}{V+Vh} \times 100$$

The volume concentration C of the particulate filler (in %), which according to the invention must be equal to at least C* in the dispersion considered, is equal to:

$$\frac{V}{V+V1} \times 100$$

It has been discovered that the translucent nature of the dispersion as defined above increases as C increases, for values of C greater than C*. Hence it is possible to adjust at will, to a certain extent, the translucency of the dispersion and hence the makeup obtained with this dispersion. In general, C is chosen such that transmission of light measured between two sheets of quartz over an optical path of 100$\mu$ of said dispersion (containing all the ingredients of this dispersion except for any volatile oils present) is equal to at least 5%, at a wavelength of 560 nm. Usually good makeup results are achieved when said transmission is between approximately 5 and 30%.

Preferably, the spherical or spheroidal particles have dimensions from 0.5 to 25$\mu$, in particular from 1 to 15$\mu$. These dimensions may be determined by quasi-elastic diffusion of light based on the volume distribution.

In general, the preparation of powders in the form of spherical or spheroidal particles is known. Moreover, such powders are already commercially available. The following may be cited as nonlimiting examples: mineral powders such as spherical silica, spherical titanium dioxides such as Spherititan (registered trademark), glass and ceramic beads sold by the 3M Company under the name Macrolites; powders of organic materials of natural origin such as cornstarch, wheat starch, rice starch, crosslinked or non-crosslinked; powders of synthetic spheronized (possibly crosslinked) polymers such as powders of the following: polyamides (for example nylon or polybetaalanine), polyethylene, polymethacrylic acids, polystyrene (crosslinked by divinylbenzene), silicone resin, PTFE (for example Fluon, particles sold by Montefluos and Hostaflon, particles sold by Hoechst), etc.

Powders of thermoplastic synthetic material in the form of hollow microspheres, which can be obtained in particular by known processes described for example in U.S. Pat. No. 3,615,972 and patent application EP-56219 may also be used. The hollow parts of these microspheres contain gas such as a hydrocarbon, air, or any other appropriate gas. The hollow miorospheres may be made of any thermoplastic material that is nontoxic and nonirritating to the skin, for example polymers or copolymers of ethylene derivatives (in particular polyethylene, polystyrene, vinyl chloride-acrylonitrile copolymers), polyamides, polyesters, urea-formaldehyde polymers, or vinylidene chloride copolymers (in particular vinylidene chloride and acrylonitrile copolymers). These hollow microspheres are very light: their specific gravity may be on the order of 0.01 to 0.1 g/cm$^3$, for example.

Binders that may be mentioned in particular are animal, vegetable, or synthetic oils, mixtures of oil(s) and wax(es), particularly mink oil, turtle oil, soybean oil, grape-seed oil, sesame oil, corn oil, colza oil, sunflower seed oil, cottonseed oil, avocado oil, olive oil, castor oil, jojoba oil, peanut oil, etc.; hydrocarbon oils such as paraffin oils, squalane, vaseline, etc.; esters such as isopropyl myristate, isopropyl palmitate, butyl stearate, hexyl laurate, isononyl isononanate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate, glycerol triisostearate, diglycerol triisostearate, etc.; silicone oils such as polymethylsiloxanes, polymethylphenylsiloxanes, polysiloxanes modified by fatty acids, polysiloxanes modified by fatty alcohols, polysiloxanes modified by polyoxyalkylenes, fluorinated silicones, etc.; perfluorated and/or organofluorated oils; higher fatty acids such as myristic acid, palmitic acid, stearic acid, behenic acid, oleic acid, linoleic acid, linolenic acid, isostearic acid, etc.; higher fatty alcohols such as cetanol, stearyl alcohol, oleic alcohol, etc.; waxes may be chosen from carnauba wax, candelilla wax, beeswax, whale wax, lanolins, microcrystalline waxes, etc.

The fatty binder may also contain volatile oils which evaporate on contact with the skin but whose presence is useful in the cosmetic composition because they facilitate spreading of the composition when applied to the skin. Such spreading agents, called "volatile oils" here, are generally oils having a saturated vapor pressure of at least 0.5 millibar (i.e. $0.5 \times 10^2$Pa) at 25° C.

When present, volatile oils generally represent less than 20% and in particular less than 10 wt. % of the final composition.

Of the volatile oils that may be present as spreading agents in the composition of the invention, silicone oils such as hexamethyldisiloxane, cyclopentadimethylsiloxane, cyclotetramethylsiloxane, fluorinated oils such as that sold under the name Galden (Montefluos), or isoparaffin oils such as those sold under the name Isopar (E, G, L or H) may be cited as examples.

Preferably the fatty binder is such that its ingredient, or the mixture of its ingredients other than the volatile oils, but including the other oil-soluble ingredients of the final composition, has a melting or softening point no greater than 37° C., in particular no greater than 32° C.

The nonvolatile fraction of the fatty binder is preferably such that its light transmission is at least 90% over an optical path of 1 cm at 560 nm.

The composition of the invention can also contain, in addition to the principal particulate filler (essentially composed of spheroidal particles as indicated above), the white or colored pigments usually used in compositions of this type. These white or colored pigments are incorporated into the dispersion described above. They preferably have particle sizes less than 1$\mu$, in particular less than 0.5$\mu$, and may range for example from 0.02 to 0.3$\mu$.

The colored pigments are in particular metal oxides such as iron oxides (yellow, red, and/or black) or chromium oxides; other metal derivatives such as titanium nitride; or organic pigments, for example melanic pigments (cuttlefish black).

The white pigments that will be cited include titanium, zinc, and zirconium oxides and also barium sulfate. These white pigments may be used in particular in combination with the colored pigments to confer consistency on the color.

In addition, all or part of the colored pigments (having their own color) may be replaced by particles colored throughout the volume of the particles.

The pigments or colored particles may be introduced into the dispersion of the invention either separately or deposited on the particles which are part of the principal particulate filler of the dispersion.

When white or colored pigments are incorporated into the dispersion, they are taken into account when determining the volume concentration of the particulate filler and when determining $C^*$.

The white and/or colored pigments, when present, represent less than 25 wt. % and generally less than 15 wt. % of the total particulate filler.

Preferably, the main additive (i.e. other than the pigments) contains no particles of lamellar shape. However, the invention extends to compositions such as those defined above also containing a minority proportion of lamellar particles (for example talc, mica, sericite, or silica), this proportion being for example such that light transmission of the dispersion obtained remains equal to at least 5%, this transmission being measured under the conditions already stated above.

The dispersion as defined above may be incorporated into a cosmetic base such as to constitute a composition in the form of a simple emulsion or a triple water-in-oil or oil-in-water emulsion or a gel.

The dispersion can also by itself constitute the composition of the invention which is then in the form of an anhydrous cosmetic such as a tinted cream, an eyeshadow, or in general in all the usual forms of cosmetic products composed of solid/liquid dispersions.

The cosmetic base may in particular include nonionic, anionic, cationic, or amphoteric surfactants. The following may be cited as examples: sugars and fatty acid esters of sugars such as sucrose, mannitol, or sorbitol esters; fatty acid esters of glycerol or polyglycerol; fatty acid esters of propylene glycol; fatty acid esters of polyoxyethylene sorbitan; fatty acid esters of polyoxyethylene sorbitol; fatty acid esters of polyoxyethylene glycerol; fatty acid esters of polyethylene glycol; polyoxyethylene alkyl ethers; polyoxyethylene phytosterols, polyoxyethylene polyoxypropylene alkyl ethers; polyoxyethylene alkyl phenyl ethers; polyoxyethylene cholestanol ethers; polyoxyethylene lanolin derivatives; polyoxyethylene alkylamines; polyoxyethylene alkylimides.

The composition of the invention can also contain various active ingredients or normal nonparticulate additives such as vitamins and their derivatives; some filters, fragrances, etc. To favor the stability of the system or produce an additional film-forming effect, a colloid may also be added, such as a polymer normally used in cosmetics, such as for example polyacrylic and polymethacrylic acids and their derivatives, particularly their esters and the corresponding copolymers; polyquaterniums; sugar polymers and gums such as celluloses and their derivatives; polyvinylpyrrolidones and their copolymers; spreading agents such as the volatile oils already cited, etc.

The compositions of the invention generally contain:
10 to 100 wt. % of said dispersion;
0 to 90 wt. % water;
0 to 10 wt. % surfactants;
0 to 40 wt. % of other normal nonparticulate active ingredients or additives.

It will be considered here that nonparticulate ingredients are those in a sufficiently divided state to have dimensions less than $0.05\mu$, in particular less than $0.02\mu$.

The cosmetics thus obtained are not covering or have only a low covering power, are translucent, and give a blurring or smoothing effect on the skin making the grain of the skin, pores, and other wrinkles less visible while retaining a natural appearance with makeup.

The invention also has as an object the use, in the preparation of a cosmetic composition able to blur defects of the skin while leaving a translucent layer thereon, of a dispersion, in a fatty binder, of a particulate filler. The particulate filler is composed of solid particles of at least one material compatible with application to the skin. The particulate filler contains at least 50 wt. %, or at least 75 vol. % relative to the total additive, of spherical or spheroidal particles with dimensions of 0.5 to $50\mu$. The particulate filler has an oil uptake such that its volume concentration $C^*$, when the binder volume is equal to that of the oil uptake, is between 3 and 90%. The volume concentration of the additive, in said dispersion, calculated without taking into account any volatile oils present in the fatty binder, is at least equal to $C^*$.

The dispersion used may have the other characteristics already described above.

Another object of the invention is a process for preparing a composition as defined above, said process being characterized by the fact that, to prepare said dispersion, the choice is made of a particulate filler composed of solid particles of at least one material compatible with application to the skin. The particulate filler contains at least 50 wt. %, or at least 75 vol. % and in particular at least 85 wt. %, relative to the total particulate filler of solid spherical or spheroidal particles having dimensions of 0.5 to $50\mu$. The particulate filler has an oil uptake such that its volume concentration $C^*$, when the volume of the binder is equal to that of the oil uptake, is between 3 and 90%, and by the fact that the volume concentration of the particulate filler, in said dispersion, measured without taking into account any volatile oils present in the fatty binder, is chosen such that it is equal to at least $C^*$.

The dispersion obtained is then brought into an appropriate form by the usual methods (addition of normal active ingredients and/or emulsification and/or packaging, etc.) to obtain the desired final cosmetic composition.

The compositions of the invention are applied to the skin in the usual way. After application, the water of the composition and any volatile oils present evaporate, leaving on the skin a thin layer composed mainly of the particulate filler of spherical particles, pigments (if any), and the nonvolatile fraction of the fatty binder.

The invention also has as its object a cosmetic treatment process allowing skin defects to be blurred in human beings, particularly the skin of the face and neck, this process being characterized by application to the skin areas treated of an effective quantity of a composition such as that defined above. The effective quantities can easily be determined by each user.

The following examples illustrate the invention without however limiting it.

EXAMPLE 1

Fluid Base

A dispersion is made of spherical silica, nylon powder, starch powder, and pigments in the relative proportions listed below, in a fatty binder such that the volume concentration of particles in the binder is equal to 80%.

The volume concentration C* of the particulate filler is 65%.

This dispersion is incorporated into water to obtain a composition with the following formula in the form of an emulsion of the oil-in-water type:

| | |
|---|---|
| Additives: | |
| Yellow iron oxide | 0.43 wt. % |
| Red iron oxide | 0.21 wt. % |
| Black iron oxide | 0.11 wt. % |
| Rutile titanium oxide | 3.25 wt. % |
| Spherical silica | 13.63 wt. % |
| Nylon powder | 6.78 wt. % |
| Starch powder | 11.44 wt. % |
| Aqueous Phase: | |
| Water | 54.40 wt. % |
| Methylparaben (preservative) | 0.30 wt. % |
| Greasy Binder: | |
| Poly(dimethylsiloxane) | 2.22 wt. % |
| Hydrogenated poly(isobutylene) | 1.92 wt. % |
| Stearyl alcohol POE (2) | 2.50 wt. % |
| Stearyl alcohol POE (21) | 2.50 wt. % |
| Propylparaben (preservative) | 0.30 wt. % |

The spherical silica used is that sold under the name SILICA BEADS SB 150 by Maprecos (size: 15μ).

The nylon powder used is that sold under the name Orgasol by ATO (size: 14.5μ).

The starch powder used is that sold under the name Dryflow by National Starch (size: 16μ).

The poly(dimethylsiloxane) is that sold under the name DC 200 Fluid 350 ct by Dow Corning.

The hydrogenated poly(isobutylene) is that sold under the name Parleam by Nichiyu.

The stearyl alcohols POE (2) and POE (21) are sold by ICI.

A makeup product of the base type applicable to the face and neck with a latex sponge for example is obtained.

When a test was run, not in public, on the application of the composition of this example 1, by a panel of women users, they declared unanimously that the covering power was low and the color was uniform; shadows under the eyes, patchiness, and any blotchiness of the skin were attenuated; the skin seemed smooth; the grain of the skin was refined. The makeup was very natural.

EXAMPLE 2

Eye Contour Cream

Similarly, a composition in the oil-in-water emulsion form was prepared, having the following formulation:

| | |
|---|---|
| Tospearl 3120 | 16.73 |
| Silica SB 150 | 18.68 |
| Water | 49.900 |
| Methyl parahydroxybenzoate | 0.300 |
| Stearyl alcohol | 0.600 |
| Cetyl alcohol | 0.600 |
| Liquid lanolin | 0.580 |
| Stearic acid | 0.290 |
| Squalene | 2.520 |
| POE (20) stearate | 2.000 |
| Self-emulsifying glycerol mono- and distearate | 2.000 |
| Propyl parahydroxybenzoate | 0.300 |
| Ammonium acrylate/acrylamide copolymer (9 wt. % aqueous emulsion) | 5.500 |
| C* = 60% | |

The volume concentration of powder in binder is 80%.

Tospearl 3120 is a trademark registered for a silicone powder sold by Toshiba (size: 12μ).

The POE (20) stearate is the commercial surfactant Mirj 49 by ICI.

The self-emulsifying glycerol mono- and distearate mixture is the commercial product Arlacel 165 by ICI.

The aqueous emulsion is sold by Hoechst.

EXAMPLE 3

"Eye Contour" Personal Care Cream

Similarly, a composition of the oil-in-water emulsion form with the following formulation was prepared:

| | |
|---|---|
| Tospearl 3120 | 34.630 |
| Water | 45.900 |
| Methyl parahydroxybenzoate | 0.300 |
| Glycerol | 2.000 |
| Polyglycerol 500 | 2.000 |
| Stearyl alcohol | 0.600 |
| Cetyl alcohol | 0.600 |
| Liquid lanolin | 0.710 |
| Squalene | 3.100 |
| Stearic acid | 0.360 |
| POE (20) stearate | 2.000 |
| Glycerol mono- and disstaerate | 2.000 |
| Propyl parahydroxybenzoate | 0.300 |
| Ammonium acrylate/acrylamide copolymer (aqueous emulsion by Hoechst) | 5.500 |
| C* = 60% | |

The volume concentration of the particulate filler in the binder is 80%.

Polyglycerol 500 is sold by Rossow.

EXAMPLE 4

Nontinted Face Cream

Similarly, a composition in the form of an oil-in-water emulsion with the following formulation was prepared.

| | |
|---|---|
| Silica SB 700 | 23.750 |
| Water | 47.900 |
| Methyl parahydroxybenzoate | 0.300 |
| Stearyl alcohol | 0.600 |
| Cetyl alcohol | 0.600 |
| Liquid lanolin | 2.580 |
| Squalane | 11.180 |
| Stearic acid | 1.290 |
| POE (20) stearate | 3.000 |
| Glycerol mono- and distearate | 3.000 |
| Propyl parahydroxybenzoate | 0.300 |
| Ammonium acrylate/acrylamide copolymer (aqueous emulsion by Hoechst) | 5.500 |
| C* = 62% | |

The volume concentration of the particulate filler in the binder is 70%.

EXAMPLE 5

Nontinted Eye Contour Cream

Similarly, a composition in the form of an oil-in-water emulsion with the following formulation was prepared.

| | |
|---|---|
| Silica SB 700 | 28.888 |
| Water | 49.900 |
| Methyl parahydroxybenzoate | 0.300 |
| Stearyl alcohol | 0.600 |
| Cetyl alcohol | 0.600 |
| Liquid lanolin | 1.700 |
| Squalane | 7.364 |
| Stearic acid | 0.848 |
| POE (20) stearate | 2.000 |
| Glycerol mono- and distearate | 2.000 |
| Propyl parahydroxybenzoate | 0.300 |
| Ammonium acrylate/acrylamide copolymer (aqueous emulsion by Hoechst) | 5.500 |
| $C^* = 60\%$ | |

The volume concentration of the particulate filler in the binder is 80%. Silica SB 700 is a silica powder sold by Maprecos (size: 16μ).

EXAMPLE 6

Nontinted Cream

A dispersion of silica in the binder (volume concentration of silica: 75%) is made, then incorporated into a water-in-oil emulsion:

| | |
|---|---|
| Silica SB 700 | 26.240 |
| Water | 53.400 |
| Methyl parahydroxybenzoate | 0.300 |
| Stearyl alcohol | 0.600 |
| Cetyl alcohol | 0.600 |
| Liquid lanolin | 2.152 |
| Squalane | 9.332 |
| Stearic acid | 1.076 |
| Dodecylglycol copolymer Methoxypolyethyleneglycol (220E) | 2.500 |
| Polyglycerol sesquioleate | 3.500 |
| Propyl parahydroxybenzoate | 0.300 |
| $C^* = 60\%$. | |

The dodecylglycol/methoxypolyethyleneglycol (220E) copolymer is sold by Akzo (Elfacos E200).

EXAMPLE 7

Nontinted Eye Contour Cream

Similarly, a composition in the oil-in-water emulsion form with the following formulation was prepared:

| | |
|---|---|
| Silica SB 150 | 36.144 |
| Water | 49.900 |
| Methyl parahydroxybenzoate | 0.300 |
| Stearyl alcohol | 0.600 |
| Cetyl alcohol | 0.600 |
| Liquid lanolin | 0.456 |
| Squalane | 1.972 |
| Stearic acid | 0.228 |
| POE (20) stearate | 2.000 |
| Glycerol mono- and distearate | 2.000 |
| Propyl parahydroxybenzoate | 0.300 |
| Ammonium acrylate/acylamide copolymer (aqueous emulsion by Hoechst) | 5.500 |
| $C^* = 41\%$ | |

The volume concentration of the particulate filler in the binder is 80%.

EXAMPLE 8

Nontinted Face Cream

Similarly, a composition in the oil-in-water emulsion form with the following formulation was prepared:

| | |
|---|---|
| Silica SB 150 | 31.840 |
| Water | 49.900 |
| Methyl parahydroxybenzoate | 0.300 |
| Stearyl alcohol | 0.600 |
| Cetyl alcohol | 0.600 |
| Liquid lanolin | 1.192 |
| Squalane | 5.172 |
| Stearic acid | 0.596 |
| POE (20) stearate | 2.000 |
| Glycerol mono- and distearate | 2.000 |
| Propyl parahydroxybenzoate | 0.300 |
| Ammonium acrylate/acrylamide copolymer (aqueous emulsion by Hoechst) | 5.500 |
| $C^* = 41\%$ | |

The volume concentration of the particulate filler in the binder is 60%.

EXAMPLE 9

Nontinted Face Cream

Similarly, a composition in the oil-in-water form with the following formulation was prepared:

| | |
|---|---|
| Silica SB 150 | 17.384 |
| Tospearl 3120 | 15.588 |
| Water | 42.90 |
| Methyl parahydroxybenzoate | 0.30 |
| Cetyl alcohol | 0.60 |
| Stearyl alcohol | 0.60 |
| Liquid lanolin | 1.004 |
| Stearic acid | 0.50 |
| Squalane | 4.344 |
| POE (20) stearate | 2.00 |
| Self-emulsifiable glycerol mono- and distearate | 2.00 |
| Propyl parahydroxybenzoate | 0.30 |
| Ammonium acrylate/acrylamide copolymer (aqueous emulsion by Hoechst) | 5.50 |
| Acrylamide/chloride copolymer of dimethyldiallyl ammonium (sold by the Merck Co. as Marquat) | 2.00 |
| Cyclopentadimethylsiloxane | 5.00 |
| $C^* = 52\%$ | |

Concentration of the particulate filler in the binder: C=70%.

EXAMPLE 10

Light Nontinted Face Cream

Similarly, a composition in the form of an oil-in-water emulsion with the following formulation was prepared:

| | |
|---|---|
| Silica SB 150 | 18.68 |
| Tospearl 3120 | 16.73 |
| Water | 42.98 |
| Methyl parahydroxybenzoate | 0.30 |
| Cetyl alcohol | 0.60 |
| Stearyl alcohol | 0.60 |
| Liquid lanolin | 0.50 |
| Stearic acid | 0.29 |
| Squalane | 2.52 |
| POE (20) stearate | 2.00 |
| Self-emulsifiable glycerol mono- and distearate | 2.00 |
| Propyl parahydroxybenzoate | 0.30 |
| Perfluoropolyether (sold by the | 2.00 |

| | |
|---|---|
| Montefluos Company under the name Fomblin HC/R) | |
| Ammonium acrylate/acrylamide copolymer (aqueous emulsion by Hoechst) | 5.50 |
| Cyclopentadimethylsiloxane | 5.00 |
| C* = 52% | |
| C = 80% | |

EXAMPLE 11

Tinted Face Cream

Similarly, a composition in the form of an oil-in-water emulsion with the following formulation was prepared:

| | |
|---|---|
| Yellow iron oxide | 0.13 |
| Red iron oxide | 0.06 |
| Black iron oxide | 0.03 |
| Titanium dioxide | 0.665 |
| Silica SB 150 | 17.92 |
| Acrylate/$C_{10}$-$C_{30}$ alkylacrylate cross-polymer | 2.00 |
| Carboxyvinyl polymer | 2.00 |
| Polyglycerol 500 | 2.00 |
| Glycerol | 2.00 |
| Methyl parahydroxybenzoate | 0.30 |
| Perfluoropolyether | 2.00 |
| Water | 48.17 |
| Sodium metaphosphate | 0.30 |
| Cetyl alcohol | 0.60 |
| Stearyl alcohol | 0.60 |
| Liquid lanolin | 0.564 |
| Stearic acid | 0.281 |
| Squalane | 2.441 |
| Propyl parahydroxybenzoate | 0.30 |
| Tospearl 3120 | 16.044 |
| Mocronized titanium dioxide | 0.665 |
| Triethanolamine | 0.930 |
| C* = 52% | |
| C = 80% | |

The polymer acrylate/$C_{10}$-$C_{30}$ alkylacrylate cross-polymer is sold by the Goodrich Company under the name Pemulen TR2.

The perfluoropolyether oil is sold by the Montefluos Company under the name Fomblin HC/R.

In the present example and following examples, unless otherwise stated the titanium dioxide has a particle size of 0.2 to 0.3µ.

EXAMPLE

Fluid Base

Similarly, a composition in the oil-in-water emulsion form with the following formulation was prepared:

| | |
|---|---|
| Yellow iron oxide | 0.60 |
| Red iron oxide | 0.39 |
| Black iron oxide | 0.11 |
| Titanium dioxide | 2.90 |
| Silica SB 150 | 21.904 |
| Water | 40.50 |
| Polyglycerol 500 | 3.50 |
| Methyl parahydroxybenzoate | 0.20 |
| Perfluoropolyether | 2.00 |
| Muscat rosebush oil | 0.276 |
| Palm oil | 0.344 |
| Parleam oil | 0.704 |
| Jojoba oil | 2.112 |
| Glyceryl mono- and distearate | 4.00 |
| Oxyethylene glyceryl monostearate (30 OE) | 4.00 |
| Propyl parahydroxybenzoate | 0.20 |
| Nylon powder | 10.660 |
| Water | 5.00 |
| Methyl parahydroxybenzoate | 0.30 |
| Fragrance | 0.30 |
| C* = 43% | |
| C = 80% | |

Glyceryl mono- and distearate is sold by the Goldschmidt Company under the name TeginM.

Oxyethylene glyceryl monostearate (30 OE) is sold by the Goldschmidt Company under the name Tagat S.

EXAMPLE 13

Base

Similarly, a composition in the form of an oil-in-water emulsion with the following formulation was prepared:

| | |
|---|---|
| Yellow iron oxide | 0.60 |
| Red iron oxide | 0.39 |
| Black iron oxide | 0.11 |
| Titanium dioxide | 2.90 |
| Silica SB 150 | 20.496 |
| Water | 30.60 |
| Polyglycerol 500 | 3.00 |
| Glycerol | 3.00 |
| Methyl parahydroxybenzoate | 0.20 |
| Perfluoropolyether | 2.00 |
| Muscat rosebush oil | 0.444 |
| Palm oil | 0.552 |
| Perleam oil | 0.136 |
| Jojoba oil | 3.40 |
| POE(20) stearate | 2.00 |
| Self-emulsifiable glycerol mono- and distearate | 2.00 |
| Tocopheryl acetate | 0.50 |
| Propyl parahydroxybenzoate | 0.20 |
| Micronized titanium dioxide | 1.00 |
| Nylon powder | 9.972 |
| Ammonium acrylate/acrylamide copolymer (6% aqueous emulsion) | 16.00 |
| Methyl parahydroxybenzoate | 0.30 |
| Fragrance | 0.20 |
| C* = 43% | |
| C = 70% | |

The micronized titanium dioxide is sold by Tayca (mean particle size: 0.015µ). In this case it plays the role of a sun filter as it absorbs ultraviolet radiation in particular.

The nylon powder is sold by Atochem under the name Orgasol (mean particle size: 14.5µ).

The so-called "muscat rosebush" oil is a commercial mixture of triglycerides of oleic, linoleic, and linolenic acids.

EXAMPLE 14

Base

A base makeup composition with the following formulation was prepared:

| | |
|---|---|
| Colored pigments (iron oxide) | 0.6 |
| Titanium dioxide | 2.4 |
| Silica | 10.0 |
| Talc | 15.0 |
| Magnesium and aluminum silicate (powder) | 0.75 |
| Expancel DE 550 | 0.3 |
| Water | 34.6 |
| Triethanolamine | 1.1 |
| Stearic acid | 2.2 |
| Glycerol | 3.0 |
| Glycerol stearate | 2.2 |

| | |
|---|---|
| Dimethicone | |
| Cyclomethicone | |
| UV filter (octyl methoxycinnamate) | 1.0 |
| Preservatives | 0.65 |
| Fragrance | 0.2 |

The silica used is that sold under the name Silicabeads SB (Myoshi).

Dimethicone is a polydimethylsioxane sold under the name Dow Corning 200 Fluid 10 cs.

Cyclomethicone is a volatile silicone oil sold under the name Dow Corning 245 Fluid.

Expancel DE 550 is the trademark designating a hollow microsphere powder sold by Kemanord Plast.

What is claimed is:

1. Cosmetic composition able to blur skin defects while leaving a translucent layer on the skin, said composition comprising a dispersion, in a fatty binder, of a particulate filler composed of solid particles of at least one material compatible with application to the skin, said particulate filler containing at least 50 wt. %, or at least 75 vol. % relative to the total particulate filler, of spherical or spheroidal particles 0.5 to 50$\mu$ in size, said particulate filler having an oil uptake such that its concentration by volume $C^*$, when the volume of binder is equal to that or the oil uptake (measured on the nonvolatile fraction of the binder), is between 3 and 90%, and the concentration by volume of the particulate filler in said dispersion measured on a nonvolatile fraction of the binder, namely without taking into account any volatile oils that may be present in the fatty binder, being at least equal to $C^*$.

2. Composition according to claim wherein said particulate filler contains at least 75 wt. % or at least 80 vol. % of said spherical or spheroidal particles relative to the total particulate filler 3. Composition according to claim wherein said particulate filler contains at least 85 wt. % or at least 90 vol. % of said spherical or spheroidal particles relative to the total particulate filler 4. Composition according to claim 1, wherein said spherical or spheroidal particles are 0.5 to 25$\mu$ in size.

5. Composition according to claim wherein said spherical or spheroidal particles have dimensions from 1 to 15$\mu$.

6. Composition according to claim 1, wherein said volume concentration $C^*$ is between 4 and 80%.

7. Composition according to claim 1, wherein a ratio between said volume concentration and concentration $C^*$ is greater than 1.

8. Composition according to claim 7, wherein said ratio is greater than or equal to 1 1.

9. Composition according to claim 8, wherein said ratio is sufficiently high for light transmission measured between two sheets of quartz over an optical path of 100$\mu$ of said dispersion (containing all the ingredients of this dispersion except for any volatile oils present) being equal to at least 5% at a wavelength of 560 nm.

10. Composition according to claim wherein said particulate filler, with the exception of any pigments present, is made only of said spherical or spheroidal particles.

11. Composition according to claim 1, wherein said particulate filler also containing a minor quantity of particles with lamellar shapes.

12. Composition according to claim wherein said material is a mineral material, an organic material of natural origin, or a synthetic polymer.

13. Composition according to claim wherein said material is chosen from silica, titanium dioxide, silicone resins, starch, polyamides, polyethylene, polymethyacrylic acids, polystyrene, optionally crosslinked, polybeta-alanine, and polytetrafluoroethylene.

14. Composition according to claim 1, wherein said particulate filler also includes a white or colored pigment.

15. Composition according to claim 14, wherein said white or colored pigment has particle sizes of less than 1$\mu$.

16. Composition according to claim 14, wherein said white or colored pigment has particle sizes of less than 0.5$\mu$.

17. Composition according to claim 14, wherein said white or colored pigment is present in a ratio of at least 25 wt. % relative to the total particulate filler.

18. Composition according to claim 14, wherein said white or colored pigment is present in a ratio of at least 15 wt. % relative to the total particulate filler.

19. Composition according to claim 1, having no white or colored pigments.

20. Composition according to claim 1, wherein the binder is an animal, vegetable or synthetic oil, a mixture of oils, or a mixture of at least one oil and at least one wax.

21. Composition according to claim wherein the nonvolatile fraction of said fatty binder has a melting or softening point no higher than 37° C.

22. Composition according to claim wherein the nonvolatile fraction of said fatty binder has a melting or softening point no greater than 32° C.

23. Composition according to claim wherein the nonvolatile fraction of the fatty binder has a light transmission at 560 nm of at least 90% over an optical path of 1 cm.

24. Composition according to claim wherein said dispersion is incorporated into a cosmetic base to constitute a water-in-oil emulsion, an oil-in-water emulsion, or a gel.

25. Composition according to claim 1, containing:
10 to 100 wt. % of said dispersion;
0 to 90 wt. % water;
0 to 10 wt. % surfactants;
0 to 40 wt. % other nonparticulate normal active ingredients or additives.

26. A method of preparation of a cosmetic composition able to blur defects of the skin while leaving a translucent layer thereon, comprising forming a dispersion, in a fatty binder, of a particulate filler composed of solid particles of at least one material compatible with application to the skin, said particulate filler containing at least 50 wt. %, or at least 75 vol. % relative to the total particulate filler, of spherical or spheroidal particles with dimensions of 0.5 to 50$\mu$, said particulate filler having an oil uptake such that its volume concentration $C^*$, when the binder volume is equal to that of the oil uptake (measured in the nonvolatile fraction of the binder), is between 3 and 90%, and the volume concentration of the particulate filler, in said dispersion, calculated without taking into account any volatile oils present in the fatty binder, is at least equal to $C^*$.

27. Cosmetic treatment process, particularly one allowing skin defects to be blurred, comprising applying to areas of skin to be treated an effective quantity of a composition as defined in claim 1.

28. Cosmetic composition able to blur skin defects while leaving a translucent layer on the skin, said composition comprising a dispersion, in a fatty binder, of a particulate filler composed of solid particles of at least one material compatible with application to the skin, said particulate filler containing at least 50 wt. %, or at least 75 vol. % relative to the total particulate filler, of spherical or spheroidal particles 0.5 to 50µ in size, said particulate filler having an oil uptake such that its concentration by volume $C^*$, when the volume of binder is equal to that of the oil uptake (measured on the nonvolatile fraction of the binder), is between 3 and 90%, the concentration by volume of the particulate filler in said dispersion, measured on a nonvoltile fraction of the binder, namely without taking into account any volatile oils that may be present in the fatty binder, being at least equal to $C^*$, and wherein the nonvolatile portion of said fatty binder has a melting or softening point no higher than 37° C.

29. A composition according to claim 28, wherein the nonvolatile portion of said fatty binder has a melting or softening point no higher than 32° C.

30. A method of preparation of a cosmetic composition able to blur defects of the skin while leaving a translucent layer thereon, comprising forming a dispersion, in a fatty binder, of a particulate filler composed of solid particles of at least one material compatible with application to the skin, said particulate filler containing at least 50 wt. %, or at least 75 vol. % relative to the total particulate filler, of spherical or spheroidal particles with dimensions of 0.5 to 50µ, said particulate filler having an oil uptake such that its volume concentration $C^*$, when the binder volume is equal to that of the oil uptake (measured in the nonvolatile fraction of the binder), is between 3 and 90%, the volume concentration of the particulate filler, in said dispersion, calculated without taking into account any volatile oils present in the fatty binder, is at least equal to $C^*$, and wherein the nonvolatile portion of said fatty binder has a melting or softening point no higher than 37° C.

31. A method according to claim 30, wherein the nonvolatile portion of said fatty binder has a melting or softening point no higher than 32° C.

32. A method of preparation of a cosmetic composition able to blur defects of the skin while leaving a translucent layer thereon, comprising selecting a particulate filler so that said particulate filler contains at least 50 wt. %, or at least 75 vol. %, relative to the total particulate filler, of spherical or spheroidal particles with dimensions of 0.5 to 50µ, so that said particulate filler has an oil uptake (measured in the nonvolatile fraction of he binder), of between 3 and 90%, selecting a volume concentration of the particulate filer, in a dispersion of he filler in a fatty binder, calculated without taking into account any volatile oils present in the fatty binder, so that said volume concentration is at least equal to $C^*$, and forming said dispersion in said fatty binder of said particulate filler.

33. Cosmetic treatment process, particularly one allowing skin defects to be blurred, comprising applying to areas of skin to be treated an effective quantity of a composition as defined in claim 28.

* * * * *